(12) United States Patent
Shao (10) Patent No.: US 7,482,593 B2
(45) Date of Patent: Jan. 27, 2009

(54) METHOD TO DETERMINE THE DEPTH-OF-INTERACTION FUNCTION FOR PET DETECTORS

(75) Inventor: Yiping Shao, Clarence, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 71 days.

(21) Appl. No.: 11/551,436

(22) Filed: Oct. 20, 2006

(65) Prior Publication Data

US 2007/0090298 A1   Apr. 26, 2007

Related U.S. Application Data

(60) Provisional application No. 60/728,488, filed on Oct. 20, 2005.

(51) Int. Cl.
*G01T 1/20* (2006.01)
(52) U.S. Cl. .................................................. 250/366
(58) Field of Classification Search ................ 250/366, 250/370.11, 363.02, 363.03, 369, 393, 367; 600/436
See application file for complete search history.

(56) References Cited

U.S. PATENT DOCUMENTS

| 4,750,972 A | 6/1988 | Casey et al. |
| 5,122,667 A | 6/1992 | Thompson |
| 5,349,191 A | 9/1994 | Rogers |
| 5,760,401 A | 6/1998 | Nelleman et al. |
| 6,140,650 A | 10/2000 | Berlad |
| 6,459,085 B1 | 10/2002 | Chang et al. |
| 6,528,793 B1 | 3/2003 | Chen et al. |
| 7,071,474 B2 | 7/2006 | Wong et al. |
| 2002/0036269 A1 | 3/2002 | Shahar et al. |
| 2003/0105397 A1* | 6/2003 | Turner et al. ................ 600/436 |
| 2005/0230626 A1 | 10/2005 | Crosetto |
| 2006/0197025 A1* | 9/2006 | Burr et al. .................... 250/366 |

OTHER PUBLICATIONS

Wang, G.-C. et al., Calibration of a PEM Detector With Depth of Interaction Measurement, IEEE Transactions on Nuclear Science, vol. 51, No. 3, pp. 775-781, Jun. 2004.
Meadors, et al.; Dual APD Array of LSO Crystals: Optimization of Crystal Surface Treatment; IEEE Transactions on Nuclear Science, vol. 49, No. 3, Jun. 2002; pp. 649-654.

\* cited by examiner

*Primary Examiner*—David P. Porta
*Assistant Examiner*—Kiho Kim
(74) *Attorney, Agent, or Firm*—Hodgson Russ LLP

(57) ABSTRACT

A three-dimensional PET detector of a type having a scintillation crystal and first and second photosensitive detectors arranged one at each opposite end face of the crystal for detecting scintillation interactions within the crystal is calibrated to determine a depth-of-interaction (DOI) function thereof by irradiating the crystal to cause a predetermined distribution of interactions along a depth axis of the crystal, and applying probability theory to signal data collected by the two photosensitive detectors. The method provides a DOI function that indicates DOI position as a function of a signal ratio R obtained from the signal data.

9 Claims, 8 Drawing Sheets

METHOD TO DETERMINE THE DEPTH-OF-INTERACTION FUNCTION FOR PET DETECTORS

CROSS-REFERENCE TO RELATED APPLICATIONS

The present application claims benefit of U.S. Provisional Patent Application No. 60/728,488 filed Oct. 20, 2005, the entire disclosure of which is hereby incorporated herein by reference.

FIELD OF THE INVENTION

The invention relates generally to the field of Positron Emission Tomography (PET) imaging and other radiation detections.

BACKGROUND OF THE INVENTION

Positron Emission Tomography (PET) has become a main stream medical imaging technique for applications in oncology, cardiology, neurology, and other medical disciplines. In a PET imaging device, pairs of gamma photons resulting from a positron-electron annihilations within a patient are detected in detectors surrounding the patient. The photons in a given pair travel in opposite directions defining a line of response (LOR), and two detectors on opposite sides of the patient generate signals that represent the respective locations of two points along the LOR. The signal information from the detectors is used to reconstruct a location of the annihilation event.

PET has experienced dramatic growth since 1998 when health insurance providers permitted the reimbursement for using PET imaging. PET has also become a widely-used and critical tool in the areas of biomedical research, drug discovery and development, and so called pre-clinical studies based on molecular imaging. However, PET has faced a fundamental technical challenge with regard to image resolution. The main technical problem is that current PET detectors can only detect two-dimensional signals (an X-Y location), and the Z location coordinate is an approximation based on the location of the detector scintillation crystal. This situation results in poor spatial resolution associated with parallax error due to the crystal penetration by energetic gamma photons. It is a recognized problem that spatial resolution suffers near the radial edges of the field-of-view (FOV), resulting in a lack of spatial resolution uniformity over the entire FOV. PET performance can be significantly improved if PET detectors can measure the Z axis location or so-called "depth-of-interaction" (DOI) of a gamma photon interaction within a detector crystal.

As a result, there have been many suggestions to develop a three-dimensional PET detector over the past decades. The most promising solution so far is to use two photon sensors, such as two avalanche photo diodes (APDs), coupled to measure the interactions from two opposite ends of a detector crystal instead of a single photon sensor from one end according to current two-dimensional detector design.

Although this new design has made significant progress, its widespread adoption may take a few more years due mainly to cost issues associated with photon sensors. But, all major vendors and leading research institutes (including Lawrence Berkeley National Laboratory) are pushing this new technology. As photon sensor technology matures and new photon sensor fabrication processes are developed, improved photon sensors are becoming available at a lower cost, and the commercial application of this three-dimensional design can be expected in the next generation of PET scanners.

Figure 1:
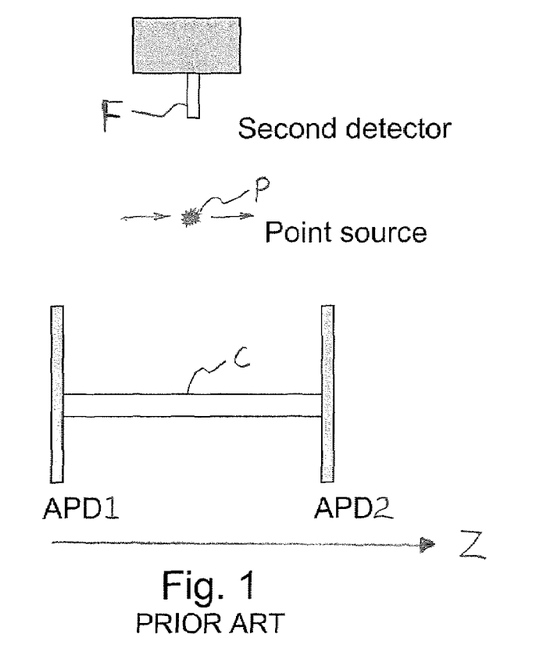
FIG. 1 is a schematic view showing a method of determining a DOI function of a PET detector in accordance with a calibration method of the prior art.

With this new PET detector design, there is one major technical challenge: it needs an efficient and accurate calibration method to determine the response function of the three-dimensional detector. Such an efficient and accurate calibration method is crucial to ensure proper functioning of the detector. Since a ratio of the signals from the two photon detectors is related to the DOI along the crystal Z axis, the DOI can be calculated based on this signal ratio if a predetermined function between the signal ratio and DOI is known. This DOI function needs to be experimentally determined through calibration. Currently, this DOI function is determined by using a point radiation source P in the middle of the primary detector crystal C (with its DOI function to be determined) and a second small size detector F, as shown in FIG. 1. A coincidence between the two detectors C and F is required to take the data so that the DOI position can be allocated. Signals are acquired from the two photon detectors APD1 and APD2, and a corresponding signal ratio is calculated for the associated DOI position. This procedure is repeated for a plurality of DOI positions along the depth (Z) axis of detector crystal C to obtain the functional relationship (DOI function) between DOI position and signal ratio. In order to measure the entire DOI function, point source P and second detector F must be moved along the depth axis of primary detector C to take multiple measurements at different DOI positions. There are several drawbacks with this method, including that it requires complicated experimental setup with an extra detector and coincidence process to allocate the DOI position; the measurement has to be taken at different DOI positions along the crystal, which requires demanding detector/source alignment and movement and lengthy time to complete; and it is potentially prone to significant measurement error due to the setup itself and size limitations of the second detector F. Moreover, the current method is simply not practical to measure the DOI functions for multiple crystals inside an array of crystals.

At present, there is no effective calibration method for such three-dimensional PET detectors. The current method described in the preceding paragraph requires a movable radiation source to be accurately aligned with the detector, which is a complicated setting, and cannot be applied to a practical detector since the inner crystals in an array cannot be calibrated. The calibration process is very long and tedious, and is not useful for practical purposes. In summary, the current method of determining a DOI function requires complicated settings for laboratory bench-top testing, and still cannot be applied to any practical detectors, or is too coarse or unstable to be used for accurate calibration required by medical industry standards.

SUMMARY OF THE INVENTION

It is an object of the present invention to provide an improved method for calibrating three-dimensional PET detectors of a type having a scintillation crystal and first and second photosensitive detectors arranged one at each opposite end face of the crystal for detecting scintillation interactions within the crystal. More specifically, it is an object of the present invention to provide a method for determining a DOI function of a PET detector that is significantly easier and faster to execute, and yields more accurate results, than prior art methods. It is ultimately a goal of the present invention to provide a calibration method that is suitable for practical use in the fields of medical and research imaging.

In summary, a method according to an embodiment of the present invention broadly comprises the steps of: irradiating a PET detector crystal to provide a predetermined distribution of scintillation interactions along a depth axis of the crystal extending between the opposite end faces of the crystal; collecting a plurality of output signal pairs each including a first output signal associated with a first photosensitive detector at one end of the crystal and a second output signal associated with a second photosensitive detector at an opposite end of the crystal, each collected output signal pair corresponding to a respective scintillation interaction at a specific DOI position z; calculating a signal ratio R for each of the plurality of output signal pairs, the signal ratio R representing a strength of the first output signal relative to the sum of the first and second output signals; and applying probability theory to the calculated signal ratios R to determine a cumulated distribution function CDF(R), the cumulated distribution function CDF(R) indicating DOI position z as a function of signal ratio R.

The method of the present invention avoids the need for an additional calibration detector and source that must be aligned and moved together in steps along the depth axis of the crystal to make many different measurements. Thus, the method of the present invention is faster and easier than prior methods. In addition, the method of the present invention yields more accurate calibration results than prior methods.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

This invention provides a new and innovative method for calibrating three-dimensional PET detectors by applying probability techniques to the problem of calibration. The method is simple, efficient, and accurate, and can be used for the development, installation, and diagnostic use of three-dimensional PET detectors. The method provides a calibration process involving only a small number of settings which can be easily made or automated if desired. Consequently, the method of the present invention will be attractive to manufacturers and users of PET imaging equipment. While the present invention is described herein with reference to detection of gamma ray interactions, it applies equally well to x-ray interactions.

The present invention requires only a stationary uniform radiation source which can be very easily set; it does not require any mechanism for moving the source or an additional detector as in other methods. Thus, the calibration method of the present invention improves efficiency and accuracy of calibration and can be used for practical detectors which consist of an array of crystals—every individual crystal can be calibrated with the same setting and method. This provides a fast and robust method for repeated measurement that is suitable for a practical detector calibration.

Figure 2:
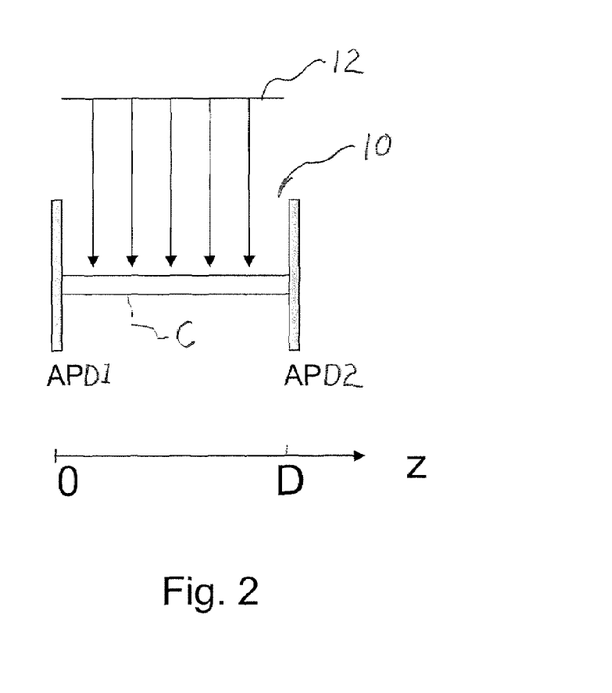
FIG. 2 is a schematic view showing a uniform irradiating step used in determining a DOI function of a PET detector in accordance with a calibration method of the present invention.

Reference is made initially to FIG. 2 of the drawings, which shows a PET detector 10 comprising an elongated narrow detector crystal C, and a pair of photon detectors embodied as avalanche photo diodes APD1 and APD2 arranged at opposite ends of crystal C. In actuality, PET detector 10 comprises a two-dimensional array of such crystals each having an associated pair of photon detectors at its opposite ends. The X-Y location of a gamma photon interaction within PET detector 10 is determined by the position of the particular crystal in the array that registers an interaction. As mentioned above, the DOI (Z axis location of the interaction) must be calculated based upon a signal ratio determined by the pair of signals generated by photon detectors APD1 and APD2. The method of the present invention determines a DOI function that computes DOI from a measured signal ratio. FIG. 2 schematically illustrates a first step according to an embodiment of the present invention, wherein detector crystal C is uniformly irradiated to have interactions uniformly distributed along the crystal depth (Z axis). Such a distribution may be provided by a uniform flood source 12 or even by a point source (not shown) at a sufficient distance from PET detector 10 to approximate a point source at infinite. It follows that the probability of an interaction, p(z), will be a constant distributed along the Z axis. Mathematically, $$\int_0^D p(z)dz = p(z)\int_0^D dz = p(z)D = 1 \tag{1}$$

where D is the total depth of crystal C, and z is the DOI position. From equation (1) we have p(z)=1/D.

The ratio of signals detected from photon detectors APD1 and APD2 is defined as $$R = g1*f1(z)/[g1*f1(z)+g2*f2(z)], \tag{2}$$

where f1(z) and f2(z) are the light collection functions of the crystal representing respective signal strength as a function depth z, and g1 and g2 are respective amplification gains, of the two photon detectors APD1 and APD2. If we define a gain ratio k=g1/g2, then equation (2) becomes $$R = k*f1(z)/[k*f1(z)+f2(z)] \quad (3)$$

A collected histogram of signal ratio R is denoted as H(R), which is a measured frequency distribution of R. A probability density function PDF(R) can be calculated from H(R) as $$PDF(R) = H(R)/\int_0^1 H(R)dR \quad (4)$$

PDF(R) is a measured probability that an interaction at DOI position z will produce the ratio of signals equal to R. If there is no signal dispersion from the detector, then there is a one-to-one pair relationship between the DOI position z and the signal ratio R, as with the probabilities p(z) and PDF(R). Therefore, we have a general formula $$\int_0^z p(z)dz = \int_0^R PDF(R)dR \quad (5)$$

Although equation (5) is valid for different DOI distributions, for uniform DOI distribution with p(z)=1/D, the left hand side of equation (5) is equal to z/D. If we define z'=z/D as a normalized depth ranging from 0 to 1, we have $$z = D*\int_0^R PDF(R)dR \quad (6)$$

or $$z' = \int_0^R PDF(R)dR \quad (7)$$

Equation (6) or equation (7) is exactly the DOI function to be determined, and its right hand side (defined as the cumulated distribution function CDF) is a function of signal ratio R, which can be easily calculated from the measurement signals generated by photon detectors APD1 and APD2. Thus, CDF(R) provides DOI for a given measured signal ratio R.

The probabilistic method of the present invention is validated by a "Monte Carlo" simulation as described below.

Figure 3:
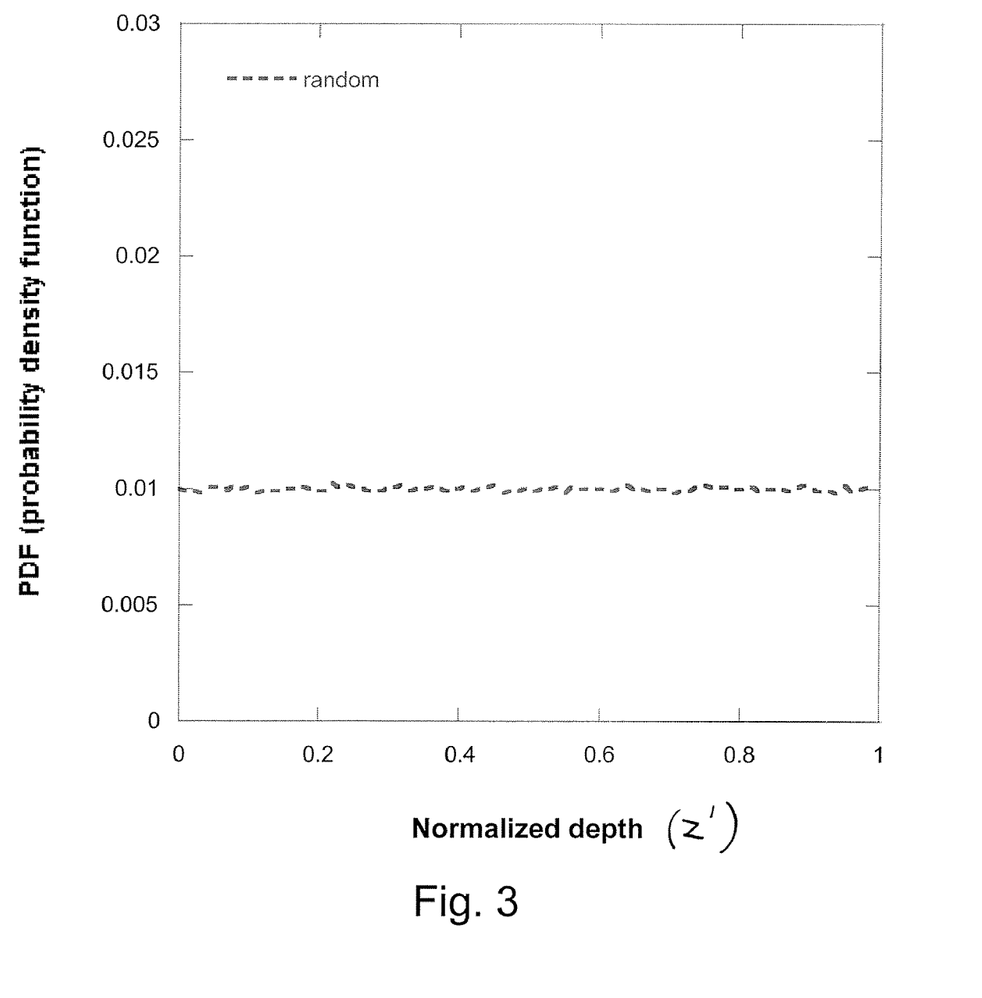
FIG. 3 is a plot showing interaction probability density as a function of normalized DOI (z') resulting from a uniform random DOI distribution generated by simulating the irradiating step of FIG. 2 in a mathematical simulation for verifying the calibration method of the present invention.

A uniform random DOI distribution is generated as shown in FIG. 3. The overall crystal depth is 30 mm.

Figure 4:
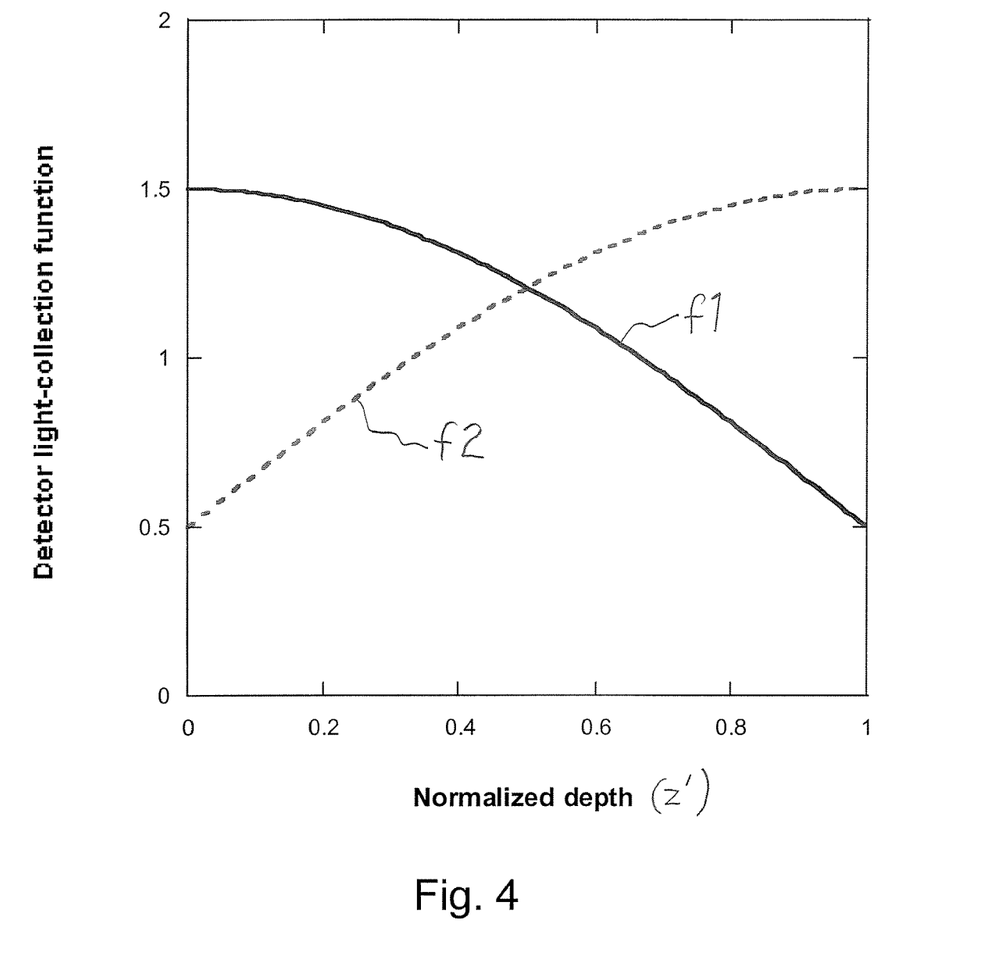
FIG. 4 is a plot showing light collection functions f1(z') and f2(z') respectively associated with photon detectors APD1 and APD2 in FIG. 2 in accordance with the mathematical simulation.

In this simulation, sinusoidal light collection functions f1(z') and f2(z') are defined as f1(z')=sin [(1−z')*π/2]+b, f2(z')=sin(z'*π/2)+b, where b=0.5 is assumed for purposes of the simulation to let the light collection efficiency vary within a factor of three at different DOI positions from one crystal end to the other, as shown in FIG. 4.

Figure 5:
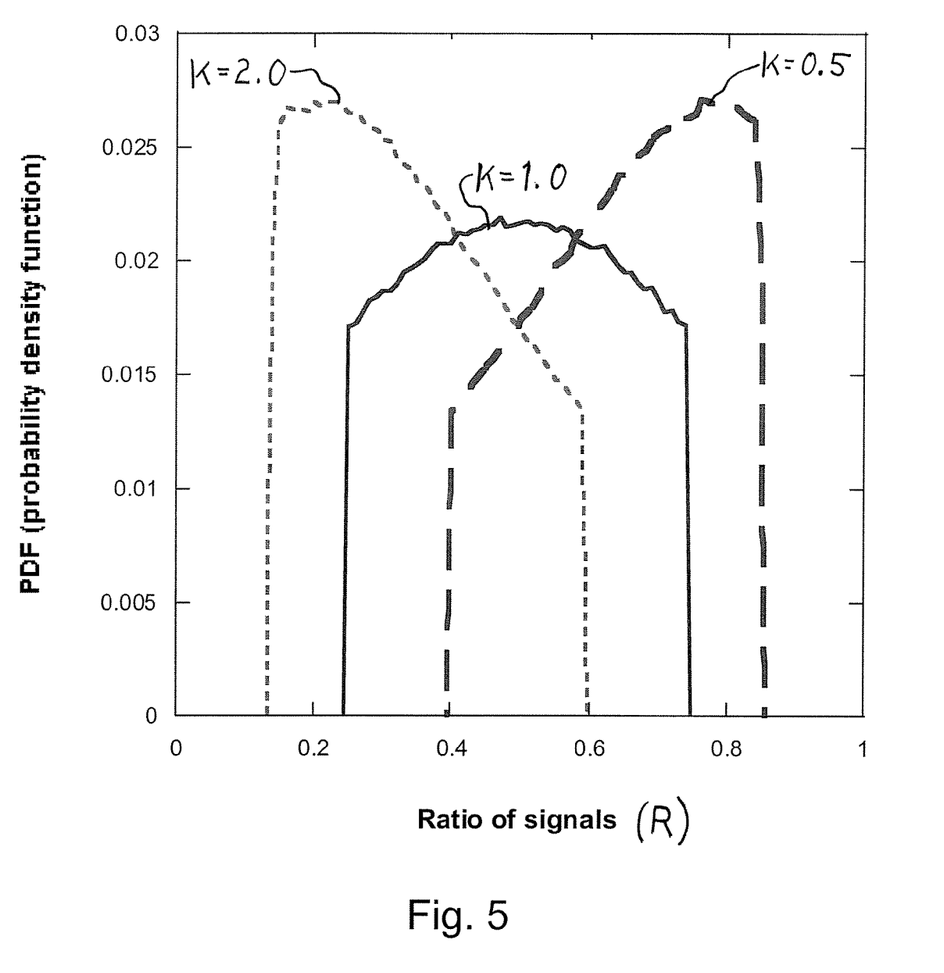
FIG. 5 is a plot showing a probability density function PDF(R) representing a measured probability that an interaction at DOI position z will produce a signal ratio R, for three different amplification gain ratios of the photon detectors APD1 and APD2, in accordance with the mathematical simulation.

FIG. 5 shows probability density functions PDF(R) for various gain ratios k=0.5, 1.0 and 2.0 to represent possible maximum 2:1 amplification gain variations between APD1 and APD2.

Figure 6:
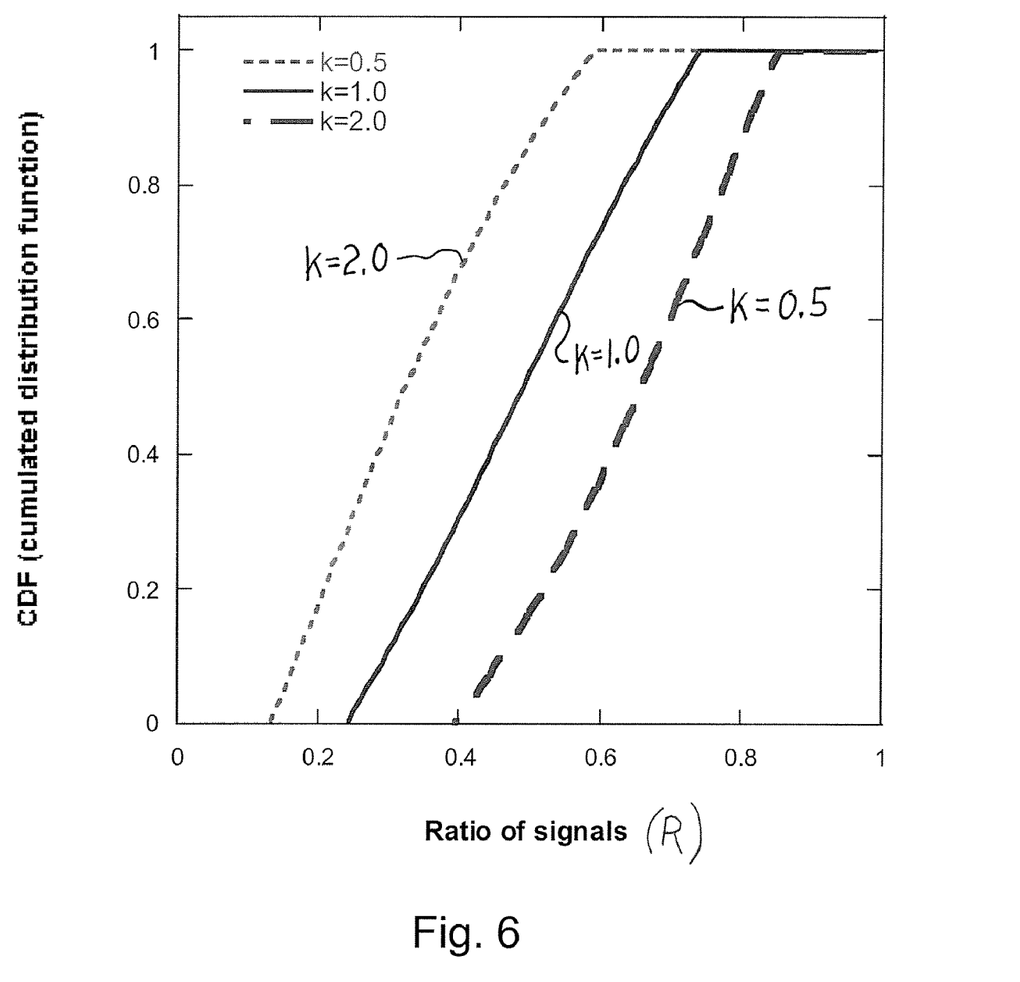
FIG. 6 is a plot showing a cumulated distribution function CDF(R) representing normalized DOI position z' as a function of signal ratio R, for three different amplification gain ratios of the photon detectors APD1 and APD2, in accordance with the mathematical simulation.

FIG. 6 shows the corresponding cumulated distribution functions $CDF(R) = \int_0^R PDF(R)dR$ for the various gain ratios k=0.5, 1.0 and 2.0.

Figure 7:
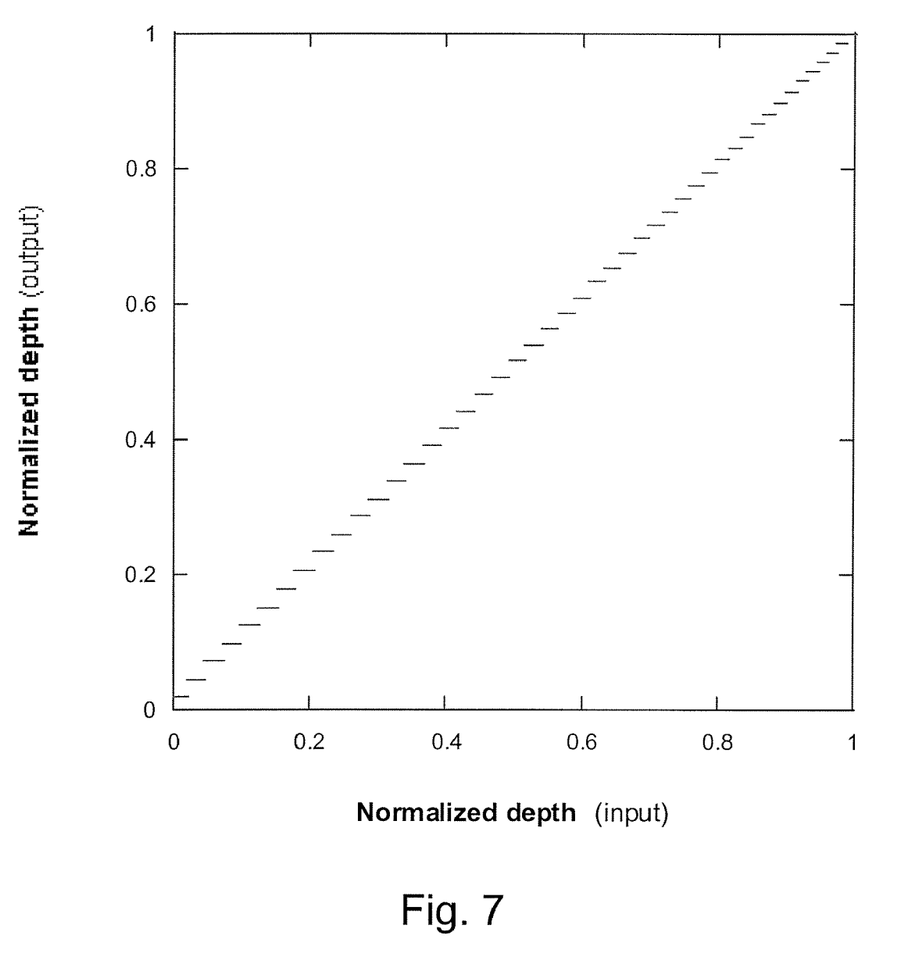
FIG. 7 is a scatter plot showing "original" normalized DOI position z' (input, horizontal axis) versus "calculated" (output, vertical axis) DOI position z' determined using the cumulated distribution function CDF(R) of FIG. 6 in accordance with the mathematical simulation.

FIG. 7 shows the scatter plot of "original" (input, horizontal axis) normalized DOI position z' versus "calculated" (output, vertical) normalized DOI position z' determined using cumulated distribution function CDF(R). There are small quantization errors (approximations due to the binning effects) in calculated z' because of the finite number of bins used in calculating R, as well as H(R), PDF(R) and CDF(R) functions. The input z' in this calculation was regenerated and is different from those being used for determining the cumulated distribution function CDF(R). Therefore, it avoided any correlations between the determination of DOI function and the afterwards calculation of DOI values using this exact DOI function.

Figure 8:
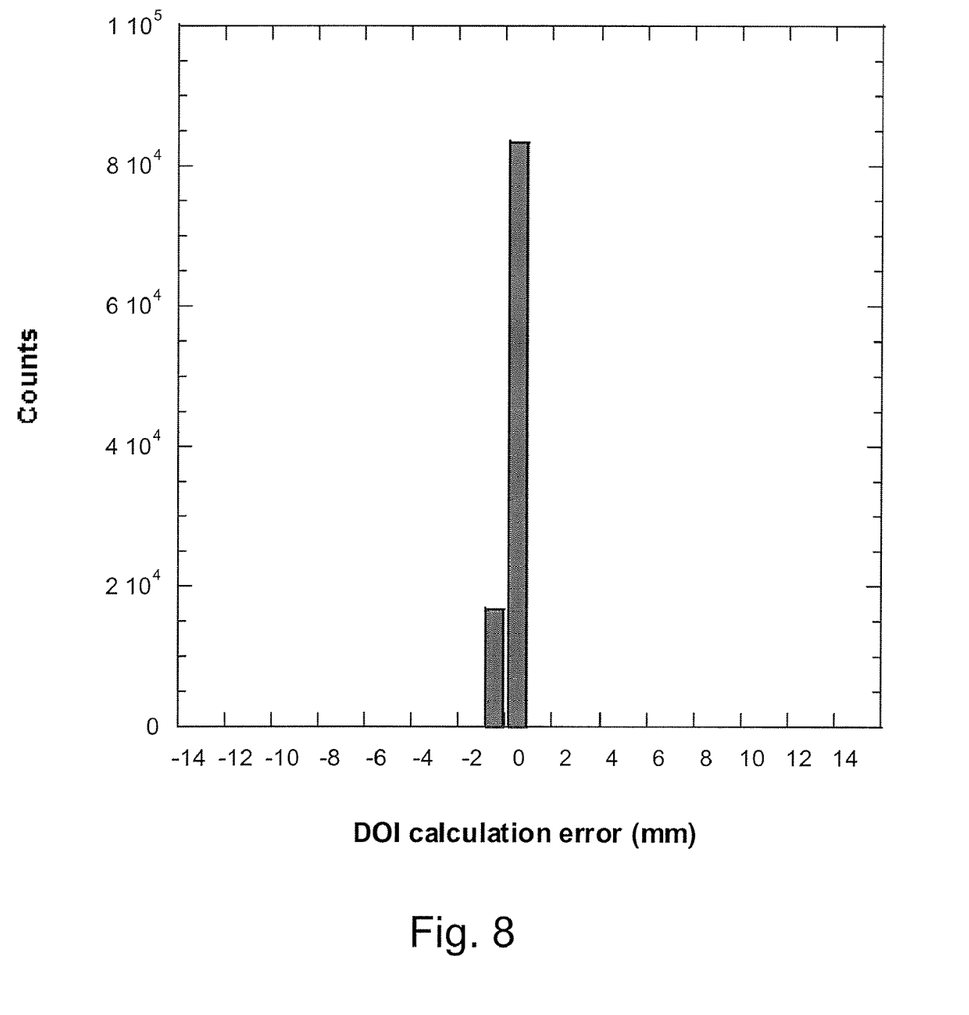
FIG. 8 is a plot showing the distribution of DOI calculation error between the input and output DOI values of FIG. 7 in accordance with the mathematical simulation.

FIG. 8 shows the distribution of DOI calculation error between the input and output DOI values.

Figure 9:
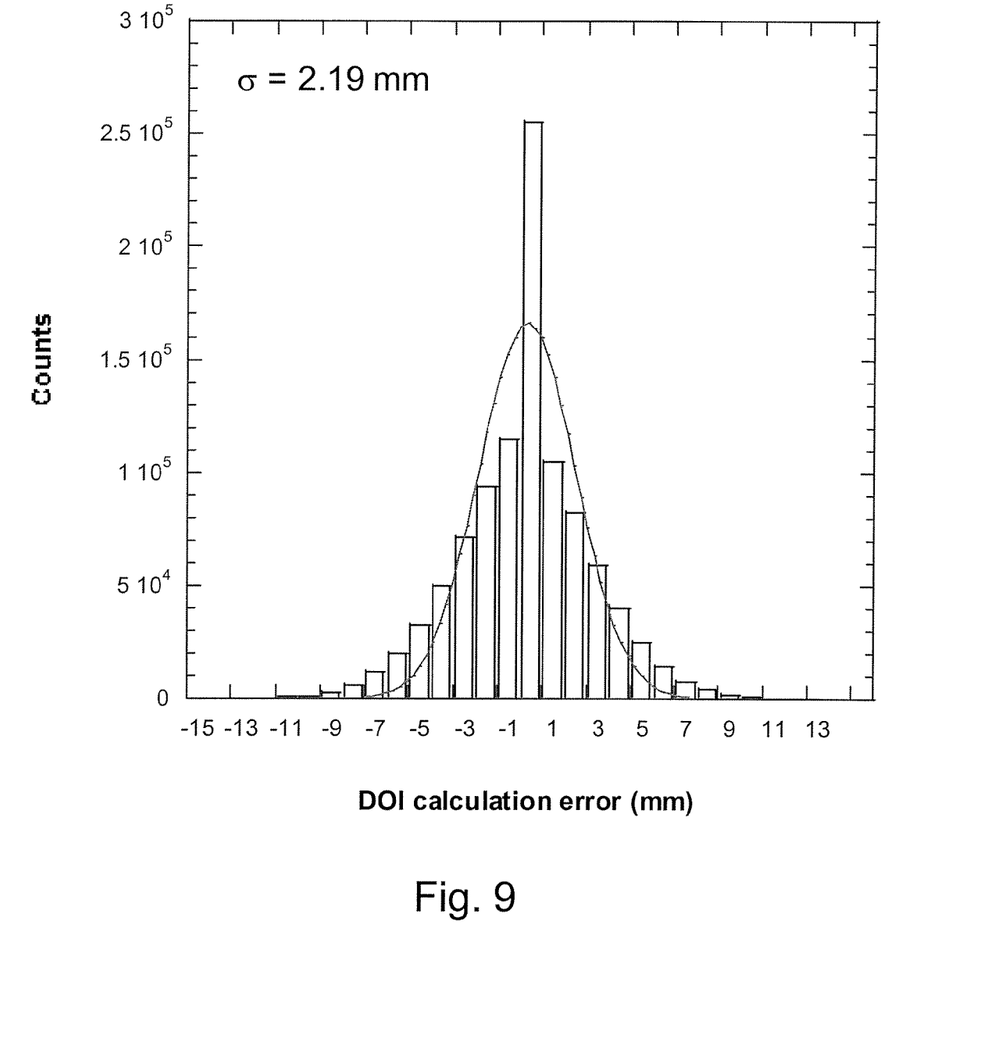
FIG. 9 is a plot showing frequency distribution of DOI calculation error in accordance with the mathematical simulation when detector signal dispersion exists.

If signal dispersion (modeled as a Gaussian function with width of sigma σ) exists, the measured error in z should be $\sqrt{2}\sigma$, because the signal will first be blurred by detector signal dispersion with one σ, then it will be processed with a DOI function (cumulated distribution function CDF(R)) that has the uncertainty equal to the same σ because the DOI function is predetermined from the signal ratios with the same Gaussian-shape dispersion. In FIG. 9, the detector signal dispersion is full-width at half-maximum FWHM=4 mm, or σ=1.70 mm. The calculated error by the new method from uniform input DOI is also a Gaussian-like function with fitted sigma σ=2.19 mm, which is approximately equal to $\sqrt{2}\sigma$. Thus, when detector signal dispersion exists as shown in any practical detector, the uncertainty of the DOI function calculated by the method of the present invention is equal to the expected uncertainty imposed by of the detector signal dispersion.

Although the DOI function is predetermined with uniform irradiation, the DOI function can be and has been calculated for several different non-uniform irradiation distributions, including exponential distributions, and they all show good agreement between the calculated and original DOI positions, within the limit imposed by detector signal dispersion.

Advantages of the new method of the present invention are very significant. The method eliminates the need to use complicated coincidence setup and multiple "step and shoot" operations across the crystal depth; the measured DOI function is a continues function without gaps; the accuracy is not limited by using an external detector size; and the setup and alignment are much easier and process is much faster compared with the current method. The method can also be used for an entire crystal array once the irradiation is uniform across the crystal depth, which can be achieved with relatively simple uniform flood source irradiation.

In practice, the DOI function initially determined for a detector may "drift" over time as the detector is used in a PET system, and recalibration becomes necessary to determine the drifted DOI function to prevent error in calculating DOI. There are two different recalibration methods that may be performed to determine a drifted DOI function:

1) For a scintillator crystal that has its internal background irradiation, if the distribution of this internal background irradiation is statistically uniform over the crystal depth axis, then it effectively provides a uniform distribution of DOI locations, so the method of invention can be directly applied for the initial calibration of DOI function or recalibration of drifted DOI function without the use of external uniform irradiation.

2) For a scintillator crystal that has no internal background irradiation, the DOI function will have to be initially determined with the method of the invention with external uniform irradiation source, for example at the detector manufacturer site. After the detector is installed inside a PET system, and when it is not possible or practical to irradiate the crystal with a uniform external source, the principle of the invention can be extended to determine a drifted DOI function in the following steps:

a) After the initial DOI function is initially determined and the detector is installed in the PET system, the detector will be irradiated with any distribution of scintillation interactions along a depth axis of the crystal extending between the opposite end faces of the crystal. This distribution of scintillation interactions is not required to be predetermined.

b) By using the equation (5), a cumulated distribution function $CDF_0(R)$ is generated that is associated with the DOI function initially determined. This cumulated distribution function $CDF_0(R)$ does not equal the DOI function because the distribution of scintillator interactions is not a uniform distribution over the crystal depth axis.

c) After the DOI function drifts during the detector operation, the detector is irradiated again with the same distribution of scintillation interactions. By using equation (5), a different cumulated distribution function $CDF_1(R)$ is generated.

d) Because in both situations the same distribution of scintillator interactions is used, the difference between the two CDF functions can only reflect the difference between the corresponding DOI functions in the same scale. The drifted or new DOI function can then be obtained by multiplying a simple multiplication factor to the initial DOI function. This multiplication factor, defined as $M(R)$, is obtained by enforcing the condition that $CDF_0(R)$ agrees with the $CDF_1(R)$, so that it will also scale the initial DOI function to the drifted DOI function. Mathematically, $M(R)=CDF_1(R)/CDF_0(R)$.

e) Once the drifted DOI function is obtained, the correct DOI values can be calculated using this new DOI function.

What is claimed is:

1. A method of determining a depth-of-interaction (DOI) function of a detector having a scintillation crystal and first and second photosensitive detectors arranged one at each opposite end face of the crystal for detecting scintillation interactions within the crystal, the method comprising the steps of:
   irradiating the crystal to provide a predetermined distribution of scintillation interactions along a depth axis of the crystal extending between the opposite end faces of the crystal;
   collecting a plurality of output signal pairs each including a first output signal associated with the first photosensitive detector and a second output signal associated with the second photosensitive detector, each collected output signal pair corresponding to a respective scintillation interaction at a specific DOI position z;
   calculating a signal ratio R for each of the plurality of output signal pairs, the signal ratio R representing a strength of the first output signal relative to the sum of the first and second output signals; and
   applying probability theory to the calculated signal ratios R to determine a cumulated distribution function $CDF(R)$, the cumulated distribution function $CDF(R)$ indicating DOI position z as a function of signal ratio R.

2. The method according to claim 1, wherein the predetermined distribution is a uniform distribution of scintillation interactions along the depth axis of the crystal.

3. The method according to claim 2, wherein the uniform distribution is generated by a uniform flood source at a fixed position.

4. The method according to claim 1, wherein the step of applying probability theory includes the substeps of:
   determining a signal ratio frequency distribution $H(R)$ based on the calculated signal ratios R;
   calculating a probability density function $PDF(R)$ based on the signal ratio frequency distribution $H(R)$, the probability density function $PDF(R)$ representing a measured probability that a scintillation interaction at a DOI position z will produce a signal ratio R; and
   calculating the cumulated distribution function $CDF(R)$ based on the probability density function $PDF(R)$.

5. The method according to claim 1, wherein the detector detects gamma rays.

6. The method according to claim 1, wherein the detector detects x-rays.

7. In a method of determining a depth-of-interaction (DOI) function of a detector having a scintillation crystal and first and second photosensitive detectors arranged one at each opposite end face of the crystal for detecting scintillation interactions within the crystal, the improvement comprising the step of:
   applying probability theory to determine a cumulated distribution function $CDF(R)$, the cumulated distribution function $CDF(R)$ indicating DOI position z as a function of a signal ratio R calculated from a first output signal and a second output signal generated by the first and second photosensitive detectors, respectively.

8. The improvement according to claim 7, wherein probability theory is applied to signal data collected from the first and second photosensitive detectors while the crystal is uniformly irradiated along a depth axis of the crystal extending between the opposite end faces of the crystal.

9. A method of determining a drifted depth-of-interaction (DOI) function of a detector having a scintillation crystal and first and second photosensitive detectors arranged one at each opposite end face of the crystal for detecting scintillation interactions within the crystal, an initial DOI function of the detector being known, the method comprising the steps of:
   a) irradiating the crystal to provide a distribution of scintillation interactions along a depth axis of the crystal extending between the opposite end faces of the crystal;
   b) collecting a plurality of output signal pairs each including a first output signal associated with the first photosensitive detector and a second output signal associated with the second photosensitive detector, each collected output signal pair corresponding to a respective scintillation interaction at a specific DOI position z;
   c) calculating a signal ratio R for each of the plurality of output signal pairs, the signal ratio R representing a strength of the first output signal relative to the sum of the first and second output signals; and
   d) applying probability theory to the calculated signal ratios R to determine a first cumulated distribution function $CDF0(R)$;
   e) repeating steps (a) through (d) after drift has occurred, including providing the same distribution of scintillation interactions along a depth axis of the crystal, to determine a second cumulated distribution function $CDF1(R)$;
   f) calculating a drift scale factor $M(R) = CDF1(R) / CDF0(R)$; and
   g) multiplying the initial DOI function by the drift scale factor $M(R)$ to obtain the drifted DOI function.

* * * * *